United States Patent [19]

Bergeron, Jr.

[11] Patent Number: 4,565,874
[45] Date of Patent: Jan. 21, 1986

[54] SYNTHESIS OF PARABACTIN AND HOMOLOGS THEREOF

[75] Inventor: Raymond J. Bergeron, Jr., Gainesville, Fla.

[73] Assignee: University of Florida, Gainesville, Fla.

[21] Appl. No.: 405,693

[22] Filed: Aug. 5, 1982

[51] Int. Cl.[4] .................................. C07D 233/24
[52] U.S. Cl. .................................................. 548/239
[58] Field of Search ........................................ 548/239

[56] References Cited

PUBLICATIONS

Bergeron, R. J. et al., J. Org. Chem., 46, pp. 4524–4529, (1981).
Elliott, D. F., J. Chem. Soc. 589, (1949), "The Stereochemistry of an Oxazoline Derivative of Threonine, Improvement of a Recent Threonine Synthesis".
Peterson, T., J. Am. Chem. Soc., (1980), 102, 7715–7718, "Structure and Behavior of Spermidine Siderosphores".

Primary Examiner—George F. Lesmes
Assistant Examiner—S. A. Gibson
Attorney, Agent, or Firm—Kerkam, Stowell, Kondracki & Clarke

[57] ABSTRACT

A compound having the structural formula:

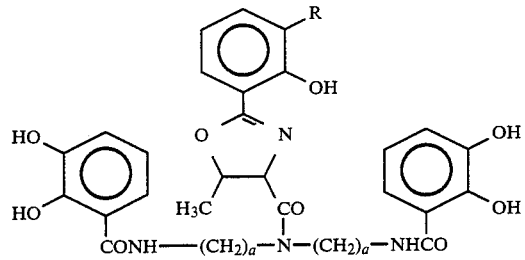

wherein R is H or OH, and a is 3 or 4.

18 Claims, 3 Drawing Figures (I)

(III)

(II)

(I)

SYNTHESIS OF PARABACTIN AND HOMOLOGS THEREOF

BACKGROUND OF INVENTION

In 1975 Tait isolated two catecholamide siderophores from *Paracoccus dentrificans* [Tait, G. H. Biochem., 146, p. 191 (1975)], namely, $N^1$, $N^8$-bis(2,3-dihydroxybenzoyl)spermidine (compound II) and $N^4$-[N-2-hydroxybenzoyl)-L-threonyl]-$N^1$,$N^8$-bis(2,3-dihydroxybenzoyl)spermidine (compound III) in FIG. 2. It was demonstrated that the former catecholamide is a biochemical precursor of the latter. Shortly after the isolation and identification of these iron sequestering agents, Jacobs and Tait [Jacobs et al, Biochem. Biophys. Res. Commun., 74, p. 1626 (1977)] demonstrated the potential of these catecholamides as therapeutic agents for the treatment of various iron overload syndromes, e.g., Cooley's anemia [Jacobs, A., Br. J. Haematol., 43, p. 1 (1979); Martell et al, Eds. "Development of Iron Chelators for Clinical Use"; Elsevier, North Holland, Inc., New York, 1981]. Compound II, a tetradentate ligand, removed iron from transferrin, one of the body's iron binding proteins, substantially better than compound III, a potentially hexacoordinate ligand. Furthermore, both of these catecholamides were more effective at removing iron from this iron shuttle protein than was desferrioximine, the clinical device currently used in chelation therapy. Unfortunately, because compounds II and III were only obtainable in milligram quantities from bacteria, a complete biological evaluation was not possible. However, these findings did generate interest in this new family of siderophores. Following Tait's discovery, a number of model catecholamide siderophores were synthesized and their binding stoichiometries as well as the thermodynamics of iron binding were evaluated: [Weitl et al, J. Am. Chem. Soc., 101, p. 2728 (1979); Carrano et al, J. Am. Chem. Soc., 101, p. 5401 (1979); Harris et al, J. Am. Chem. Soc., 101, p. 6534 (1979); Weitl et al, J. Am. Chem. Soc. 102, p. 2289 (1980); Weitl et al, J. Org. Chem., 46, p. 5234 (1981)]. However, neither compound II or III was actually synthesized until recently [Peterson et al, Tetrahedron Lett. 4805 (1979); Bergeron et al, J. Org. Chem., 45, p. 1589 (1980); Bergeron et al, J. Med. Chem., 23, p. 1130 (1980)].

It is peculiar, however, that nature should produce a structurally more complicated, less effective iron chelator (III) from a less complicated, more effective chelator (II). However, Peterson et al [Tetrahedron Lett., 4805 (1979); and Peterson et al, J. Am. Chem. Soc., 102, p. 7715 (1980)] demonstrated that this seeming inefficiency could be explained by reconsidering Tait's original proof of structure for compound III. They demonstrated that the group fixed to the central nitrogen of the sperimidine backbone was not an N-2-hydroxybenzoyl-L-threonyl moiety but rather a 2-hydroxyphenyl-4-carboxyl-5-methyl-2-oxazoline, i.e., compound I of FIG. 3, and that this oxazoline ring was opened to the threonyl compound under the acidic conditions of Tait's isolation procedure. In the oxazoline or closed form, compound I represents a hexacoordinate Fe (III) binding ligand which, in fact, binds Fe (III) tighter than either compound II or compound III.

Synthesis of compound II and analogs thereof have previously been suggested. See [Bergeron et al, J. Org. Chem. 45, p. 1589 (1980); Bergeron et al, J. Med. Chem., 23, p. 1130 (1980); Bergeron et al, J. Org. Chem., 18, p. 3712 (1981); and Bergeron et al, J. Org. Chem., 46, p. 4524 (1981)]. These catecholamides have been shown to be potent iron chelators, and effective for removing iron from iron overloaded animals.

It is an object of the present invention to provide a method for the synthesis of the compounds represented by formula (I).

BRIEF DESCRIPTION OF THE DRAWINGS

The attached drawings illustrate an embodiment of the present invention wherein.

SUMMARY OF THE INVENTION

Figure 1:
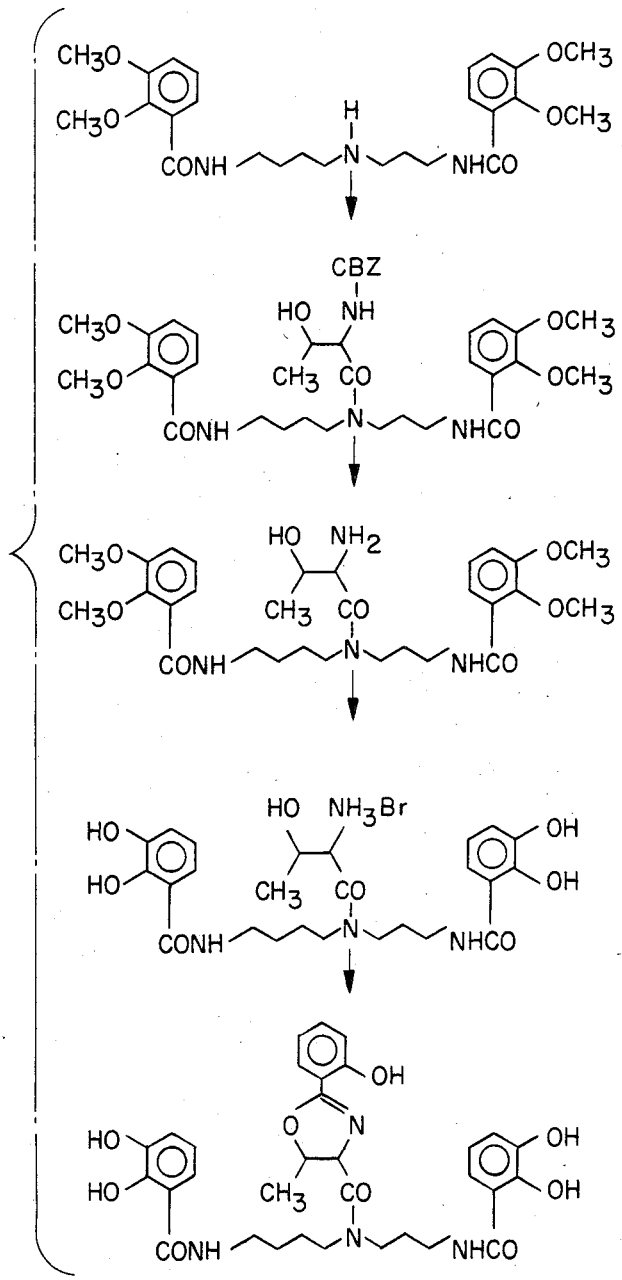
FIG. 1 depicts the reaction scheme as to the preparation of compound I.
Figure 2:
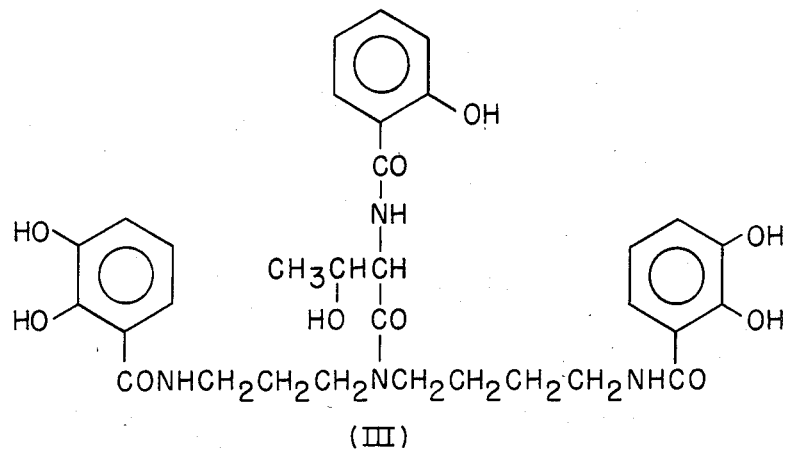
FIG. 2 depicts two isolated catecholamine siderophores.
Figure 2:
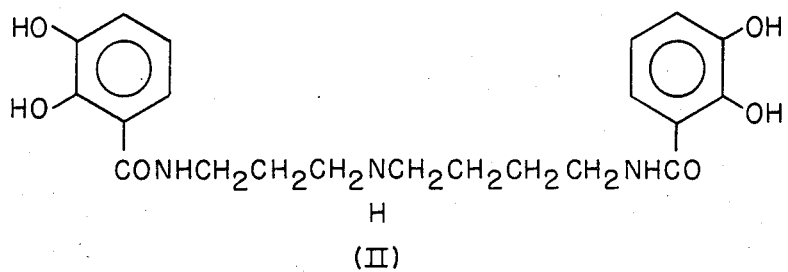
Figure 3:
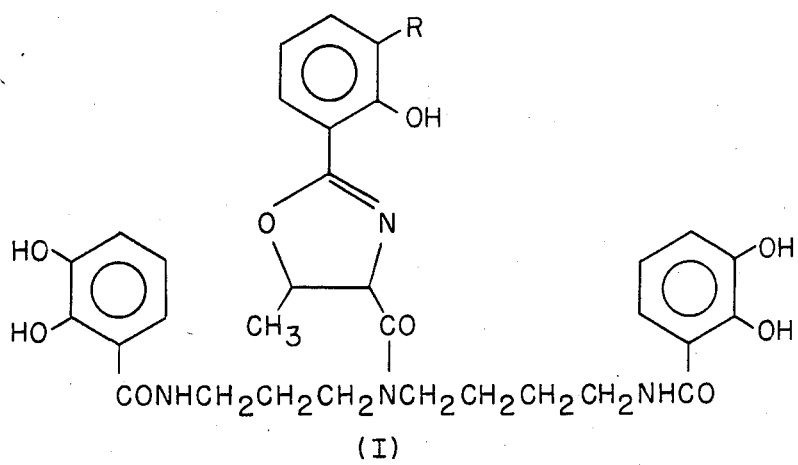
FIG. 3 depicts the structure of compound I.

The method according to the present invention is embodied in the reaction scheme set forth in FIG. 1. FIG. 1 depicts the reaction scheme as applied to the preparation of compound (I) wherein the backbone polyamine is spermidine, i.e., a compound of the formula:

It will be understood by those skilled in the art that the same reaction scheme is also applicable for the preparation of compound (I) wherein the backbone polyamine is homospermidine having the formula:

and norspermidine having the formula:

The method comprises the sequential steps (a) reacting N,N-bis(2,3-dimethoxybenzoyl)-spermidine, -homospermidine or -norspermidine with N-Z-L, D- or DL-threonine, wherein Z is a nitrogen protective group, to produce N'-(N-Z-L-, D- or DL-threonyl)-N,N-bis(2,3-dimethoxybenzoyl)-spermidine, -homospermidine or -norspermidine;

(b) removing the nitrogen protective group, Z, from the threonyl moiety to produce N'-(-, D- or DL-threonyl)-N,N-bis(2,3-dimethoxybenzoyl)-spermidine, -homospermidine or -norspermidine;

(c) demethylating the ether product of step (b) to produce N'-(L-, D- or DL-threonyl)-N,N-bis(2,3-dihydroxybenzoyl)-spermidine, -homospermidine or -norspermidine;

(d) coupling the product of step (c) with 2-hydroxybenziminoethyl ether or 2,3-dihydroxybenziminoethyl ether to produce the compound (I).

DETAILED DESCRIPTION OF THE INVENTION

In the following description the term, "spermidine", is employed for the purpose of brevity to define the polyamine backbone of the various starting materials, intermediates and final products. It is to be understood that in each such instance the polyamines homospermidine and norspermidine could also be employed as backbones.

Furthermore, when referring to the primary nitrogen atoms of the various polyamine backbones, the symbol, N, is employed. When referring to the secondary nitrogen atom of the polyamine backbones, the symbol, N', is employed.

The synthesis begins with N,N-bis(2,3-dimethoxybenzoyl)spermidine, a versatile reagent for the generation of spermidine catecholamines. The reagent may be prepared according to the method of [Bergeron et al, J. Org. Chem., 46, p. 4524 (1981)]. This compound is preferably coupled with N-carbobenzoxy-L-, D- or DL-threonine via the N-hydroxysuccinimide ester. Although the carbobenzoxy group is preferred, it will be understood that any suitable nitrogen protective group may be employed, e.g., t-butoxycarbonyl-, etc. The reagent is reacted with N-carbobenzoxy-L-, D- or DL-threonine and the condensing reagents dicyclohexylcarbodiimide and N-hydroxysuccinimide, optionally in the presence of a catalyst, such as a tertiary amine, e.g., triethylamine in an inert solvent, e.g, dimethylformamide, dioxane, acetonitrile or tetrahydrofuran (0° C.) to produce the secondary N'-acylated product, N'-(N-carbobenzoxy-L-, D- or DL-threonyl)-N,N-bis(2,3-dimethoxybenzoyl)spermidine, in 90% isolated yield. The threonyl amide intermediate was easily purified by silica gel chromatography, eluting with 5% MeOH in EtOAc. The carbobenzoxy protecting group was next removed quantitatively by reduction, preferably by hydrogenolysis over $PdCl_2$ in methanol/HCl for 24 hours, thereby producing N-L-, D- or DL-threonyl-N,N-bis(2,3-dimethoxybenzoyl)spermidine. The methanol was removed under vacuum, the residue dissolved in water and the aqueous mixture washed with chloroform. The water was removed under vacuum, the residue dissolved in chloroform and washed with aqueous sodium carbonate. The compound may be purified on silica gel. The most revealing $^1$H nmr features at 60 MHz in $CDCl_3$ were the absence of the benzyl methylene at 4.82 δ and the simplicity of the aromatic region. The envelope of complex peaks extending from 6.62–7.70 δ in (1) corresponding to eleven aromatic protons was simplified to two signals, one at 6.70–7.10 δ (4H) and one at 7.28–7.66 δ (2H). The low field signal corresponds to the ortho protons of the 2,3-dimethoxybenzoxy groups and the high field signal to the meta and para protons. The methyl protecting groups of the intermediate ether were removed preferably in quantitative fashion by reacting the amide with $BBr_3$ in $CH_2Cl_2$ at 0° C. for 6 hours. The product is hydrolyzed with methanol generating the free catechol, N'-L-, D- or DL-threonyl-N,N-bis(2,3-dihydroxybenzoyl)spermidine.HBr. The product was chromatographed on Sephadex LH-20, eluting with 20% ethanol in benzene. At 60 MHz the most outstanding $^1$H nmr feature was the absence of the —$OCH_3$ signal at 3.56 δ.

The final and most critical step in the procedure involves the coupling of 2-hydroxybenziminoethyl ether or 2-dihydroxybenziminoethyl ether [Easson et al, J. Chem. Soc., 2991 (1931)] with the free catechol. It is evident that a consideration of both the stereochemistry and acid sensitivity of the oxazoline ring system is critical to the development of such a method. Peterson et al [J. Am. Chem. Soc., 102, p. 7715 (1980)] showed that the hydrogens of the oxazoline ring system were trans to each other. It was also clear from this work that the oxazoline ring was acid labile. This meant that the synthesis must employ a stereospecific procedure as well as a sequence in which there were no steps involving acid after the introduction of the oxazoline ring. In an earlier study, Elliott [Elliott, D. F., J. Chem. Soc., 589 (1949)] demonstrated that benziminoethyl ether could be coupled with D,L-threonine ethyl ester to generate a trans-4-carboethoxy-2-phenyl-5-methyl-$\Delta^2$-oxazoline. It was primarily determined that 2-hydroxybenziminoethyl ether could be condensed with D,L-serine methylester.HCl in the presence of catechol to produce the corresponding 4-carbomethoxy-2-hydroxyphenyl-$\Delta^2$-oxazoline in 80% yield. This implied that the above produced intermediate catechols would not interfere with the desired condensation, a feature critical to the method of the invention. The actual reaction was carried out in 70% yield by refluxing the catechol and 2-hydroxybenziminoethyl ether in methanol for 24 hours and the product purified on Sephadex LH-20 (20% ethanol in benzene). The structure of the final product was verified by a high field $^1$H nmr study.

In the course of analyzing the 300 MHz $^1$H nmr spectrum of the compound based on spermidine, two structural features of the natural product observed by Peterson et al, supra, must be kept in mind, i.e., the trans hydrogens of the oxazoline ring and the conformer populations. Although Peterson et al did not provide a comparison of the so-called parabactin (compound I wherein R is H) and parabactin A (compound III) $^1$H nmr spectra, he did provide a rather exhaustive analysis of the agrobactin (compound I wherein R is OH) and agrobactin A (compound III containing two OH groups in the threonyl moiety) spectra. This information has made it possible to determine whether or not the observed parabactin $^1$H spectrum was indeed that of the oxazoline system. A comparison of the methine and methyl signals of agrobactin with its open form agrobactin A in 10/1 $CDCl_3/d_6$-DMSO point out some revealing differences. The α-proton multiplet of agrobactin is centered at 4.6 δ with a $J_{\alpha,\beta}=6.8$ Hz while the α-proton multiplet of agrobactin A is centered at 4.2 and 5.4 δ, respectively. The methyls of agrobactin and agrobactin A are centered at 1.4 δ with $J_{\gamma,\beta}=2.4$ Hz. The β-proton multiplets of the open and closed forms are centered at 4.2 and 5.4 δ, respectively. The methyls of agrobactin and agrobactin A are centered at 1.4 δ with $J_{\gamma,\beta}=6.4$ Hz and 1.2 δ with $J_{\alpha,\beta}=6.1$, respectively. Finally, what is most notable about the α and γ protons is that their signals exist "in duplicate". This was attributed to the siderophore existing in separated conformations separated by an 18 kcal/mole energy barrier. Clearly, very similar differences and/or similarities could be expected for the parabactin and parabactin A systems. This expected extension is strongly supported by the remarkable similarities in the agrobactin and parabactin oxazoline ring system spectra. The reported parabactin numbers for the α,β and γ hydrogens are 4.6 δ, J=6.8 Hz, 5.3 δ and 1.4 δ, J=6.4 Hz, respectively.

The 300 MHz $^1$H nmr spectrum of synthetic parabactin is extremely sensitive to solvent and temperature changes, e.g., when run in $d_6$-DMSO the spectrum is substantially simpler than when run in $CDCl_3$ or 10/1 $CDCl_3/d_6$-DMSO. In fact, the simplicity of the spectrum in $d_6$-DMSO is deceptive and those skilled in the art must take care to use the same solvent and temperature when comparing results. When the $^1$H nmr of parabactin is run in $d_6$-DMSO at 23° C. the γ-methyl, i.e., the methyl fixed to the oxazoline ring corresponds to four lines, two sets of doublets, one centered at 1.40 δ and one centered at 1.36 δ with $J_{\gamma,\beta}=6.3$ Hz. In $d_6$-DMSO at 23° C. the α-methine signals are centered at 4.89 δ and consist of five lines. On changing the solvent to 10/1 CDCl$_3$/d$_6$-DMSO in order to avoid the line broadening problems associated with low temperature induced viscosity changes with d-DMSO the spectrum revealed several additional lines at 23° C. The α-methine multiplet was not centered at 4.59 δ although it still consisted of five lines. However, the γ-methyl signal now consisted of six lines, three sets of doublets with identical coupling constants. Furthermore, when the sample cooled to −13° C. the five lines of the α-methine become six lines, three sets of doublets, with identical coupling constants J=6.5 Hz. The γ-methyls are not nearly as sensitive to cooling. When the β-methine is decoupled the five α-methine lines collapse to three lines just as the six γ-methyl lines collapse to three lines. Furthermore, and as expected under these decoupling conditions, when the sample is heated to 110° C. in d$_6$-DMSO and the now three lines of the α-methine and two lines of the γ-methyls coalesce to single lines. These results are, of course, in complete accord with the concept of different conformers [Peterson et al, J. Am. Chem. Soc., 102, p. 7715 (1980); and van der Helm et al, J. Am. Chem. Soc., 102, p. 7719 (1980)]. Because of the complexity of the β-methine signals, temperature experiments were not overly revealing although decoupling experiments clearly demonstrated its coupling to the α-methine and γ-methyl protons.

The remainder of the spectrum, when taken in 10/1 CDCl$_3$/d$_6$-DMSO is as expected. The six internal methylene protons of the spermidine backbone are in an envelope 2.03–1.48 δ while the eight amide methylene protons are under a 3.78–3.11 δ envelope. The β-proton signal is a complex envelope extending from 5.45–5.28 δ. The aromatic proton signals consist of five well separated envelopes, 6.52–6.67 δ (2H), 6.78–6.92 δ (4H), 7.06–7.15 δ (2H), 7.27–7.35 δ (1H), 7.51–7.71 δ (1H). Finally, the NH and OH protons are as described by Peterson with the NH and nonhydrogen bonded OH protons at 7.89–8.17 δ and the hydrogen bonded protons 11.56–12.82 δ.

As stated above, the procedure described hereinbefore may also be employed to produce the corresponding compounds (I) wherein the backbone polyamine is homospermidine or norspermidine.

The invention is illustrated by the following non-limiting examples.

EXAMPLE 1

(L)-N$^4$-[N-(tert-carbobenzoxythreonyl)]-N$^1$,N$^8$-bis(2,3-dimethoxybenzoyl)spermidine (I)

A solution of N-carbobenzoxy-L-threonine) (1.19 g, 4.7 mmol) and N-hydroxysuccinimide (0.54 g, 4.7 mmol) in THF (100 ml) was cooled to 0° C. Dropwise addition of dicyclohexylcarbodiimide (DCC)(0.97 g, 4.7 mmol) in THF (25 ml) was completed over 1 hour and the mixture allowed to warm slowly to room temperature with stirring. The mixture was then cooled to 0° C. and a solution of N$^1$,N$^8$-Bis)2,3-dimethoxybenzoyl)spermidine (2.18 g, 4.0 mmol) in THF (75 ml) was added slowly. After 48 hours the solvent was evaporated, the residue dissolved in CH$_2$Cl$_2$ (100 ml), washed with cold 3% (w/v) aqueous HCl (3×30 ml), and cold water (3×30 ml), dried, filtered and evaporated. Silica gel chromatography (5% MeOH/EtOAc) yield the product as a white, hygroscopic solid: 2.28 g (70%); $^1$H NMR (CDCl$_3$) δ 1.16 (3H, CH$_3$—), 1.58 (6H, —CH$_2$—), 3.42 (8H, —CH$_2$—), 3.56 (12H, —OCH$_3$), 4.00–4.60 (3H, 2-CH—, OH), 4.82 (2H, —CH$_2$—), 5.85–6.30 (1H, NH) 6.62–7.70 (11H, Ar), 7.70–8.40 (2H, —N—H).

Anal. calcd. for C$_{37}$H$_{48}$N$_4$O$_{10}$: C, 62.70; H, 6.83; N, 7.90. Found: C, 62.69; H, 6.76; N, 7.78.

L-N$^4$-Threonyl-N$^1$,N$^8$-bis(2,3-dimethoxybenzoyl)spermidine (2)

To a solution of (I) (5.0 g, 7.05 mmol) in MeOH (50 ml) was added HCl (0.51 g, 14.1 mmol), and PdCl$_2$ (0.5 g, 2.82 mmol). The mixture was filtered, the solvent evaporated, and the residue dissolved in CH$_2$Cl$_2$ (100 ml) and washed with cold aqueous 15%(w/v) sodium carbonate (3×100 ml). The organic phase was dried, filtered and evaporated and the residue chromatographed on silica gel (10% MeOH/CHCl$_3$) providing the product as a white gum: 3.94 g (97%); $^1$H NMR (CDCl$_3$) δ 1.10–1.20 (3H, —CH$_3$), 1.43–2.00 (6H, —CH$_2$—), 2.94–4.08 (25H, —OCH$_3$, 2-CH—, —OH, —CH$_2$—), 6.84–8.25 (8H, Ar, NH).

Anal. calcd. for C$_{29}$H$_{42}$N$_4$O$_8$: C, 60.61; H, 7.37; N, 9.75. Found: C, 60.50; H, 7.36; N, 9.62.

L-N$^4$-Threonyl-N$^1$,N$^8$-bis(2,3-dihydroxybenzoyl)-sperimidine-hydrobromide (3)

To a 1M stirred solution of BBr$_3$ (20 ml, 20.0 mmol) in dry CH$_2$Cl$_2$ (30 ml) at 0° C. was added 2 (0.83 g, 1.44 mmol) in CH$_2$Cl$_2$ (30 ml) dropwise under N$_2$. The reaction mixture was allowed to warm slowly to room temperature. After 12 hours, the reaction vessel was cooled to 0° C., and ice-cold water (25 ml) was added dropwise with vigorous stirring. The resulting suspension was allowed to warm to room temperature with continued stirring over 2 hours and the product collected by filtration. The residue was dissolved in MeOH and evaporated. This process was repeated several times. Chromatography on Sephadex LH-20 (20%→40% EtoH/benzene) gave 0.82 g (95%) of 3 as a white solid. $^1$H NMR (CO$_3$OO) δ1.10–1.37 (3H, —CH$_3$—) 1.43–2.23 (6H, —CH$_2$—), 3.13–3.80 (8H, —CH$_2$—), 3.83–4.40 (3H, 2-CH—, OH), 6.33–7.33 (6H, Ar).

Anal. calcd. for C$_{25}$H$_{35}$N$_4$O$_8$Br: C, 50.09; H, 5.88, N, 9.35. Found: C, 49.98; H, 5.96, N, 9.27.

L-(N-[3-(2,3-dihydroxybenzamido)propyl)]-N-[4-(2,3-dihydroxybenzamido)butyl]-2-(2-hydroxybenzamido)-butyl]-2-(2-hydroxybenyl)-trans-5-methyloxazoline-4-carboxamide (Parabactin)(4)

A solution of 3 (0.35 g, 0.59 mmol) and ethyl 2-hydroxybenzimidate (0.11 g, 0.67 mmol) in dry MeOH (50 ml) was heated to reflux. After 24 hours the solvent was evaporated and the residue chromatographed on Sephadex LH-20 (20% EtOH/benzene) providing 0.31 g (85%) of 4 as a white solid: $^1$H NMR (10:1, CDCl$_3$: d$_6$-DMSO) δ 1.34–1.45 (3H, —CH$_3$), 1.48–2.03 (6H, —CH$_2$—), 3.11–3.78 (8H, —CH$_2$—), 4.59 (1H, —CH—), 5.28–5.45 (1H, —CH—), 6.52–7.71 (10H, Ar), 7.89–8.17 (4H, —NH—, —OH), 11.56–12.82 (3H, —OH).

Anal. calcd. for C$_{32}$H$_{36}$N$_4$O$_9$: C, 61.93; H, 5.85; N, 9.03. Found: C, 61.93; H, 5.94; N, 8.96.

EXAMPLE 2

The procedure of Example 1 was repeated, employing ethyl 2,3-dihydroxybenzimidate to produce L-(N-[3-(2,3-dihydroxybenzamido)-propyl]-N-[4-(2,3-dihydroxybenzamido)-butyl]-2-(2,3-dihydroxyphenyl)-trans-5-methyloxazoline-4-carboxamide (agrobactin) in equivalent yields.

I claim:
1. A method for the preparation of a compound having the structural formula:

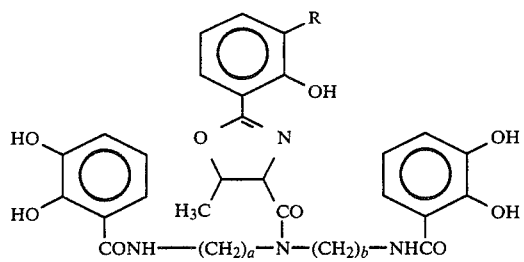

wherein R is H or OH,
a is 3 or 4, and
b is 3 or 4
comprising the sequential steps:
(a) reacting N,N-bis(2,3-dimethoxybenzoyl)-spermidine, -homospermidine or -norspermidine with N-Z-L-, D- or DL-threonine, wherein Z is a nitrogen protective group, to produce N'-(N-Z-L-, D- or DL-threonyl)-N,N-bis(2,3-dimethoxybenzoyl)-spermidine, -homospermidine or -norspermidine;
(b) removing said nitrogen protective group, Z, from said threonyl moiety to produce N'-(L-, D- or DL-threonyl)-N,N-bis(2,3-dimethoxybenzoyl)-spermidine, -homospermidine or -norspermidine;
(c) demethylating the ether product of step (b) to produce N'-(L-, D- or DL-threonyl)-N,N-bis(2,3-dihydroxybenzoyl)-spermidine, -homospermidine or -norspermidine;
(d) coupling the product of step (c) with 2-hydroxybenziminoethyl ether or 2,3-dihydroxybenziminoethyl ether to produce compound (I).

2. The method of claim 1 including the step of isolating and purifying the product of step (d).
3. The method of claim 2 wherein said product of step (d) is isolated and purified by affinity chromatography.
4. The method of claim 1 wherein the reaction of step (a) is conducted in an inert solvent at a low temperature in the presence of condensing reagents dicyclohexylcarbodiimide and N-hydroxysuccinimide.
5. The method of claim 4 wherein said inert solvent is tetrahydrofuran, dioxane or acetonitrile.
6. The method of claim 4 wherein said reaction of step (a) is conducted at about 0° C.
7. The method of claim 4 wherein the reaction of said step (a) is conducted in the presence of a tertiary amine catalyst.
8. The method of claim 1 wherein said nitrogen protective group is carbobenzoxy or t-butoxycarbonyl.
9. The method of claim 8 wherein said nitrogen protective group is removed from step (b) by reduction.
10. The method of claim 9 wherein said reduction is effected by hydrogenolysis.

11. The method of claim 10 wherein said hydrogenolysis is conducted in methanolic hydrochloric acid over palladium chloride.
12. The method of claim 1 wherein said demethylation of step (c) is effected by reaction of the ether product of step (b) with $BBr_3$ followed by hydrolysis to produce the free catechol as a hydrobromide salt.
13. The method of claim 12 including the step of converting the hydrobromide salt to the free amine.
14. The method of claim 1 wherein the coupling reaction of step (d) in an inert solvent.
15. The method of claim 14 wherein said solvent is methanol.
16. A compound having the structural formula:

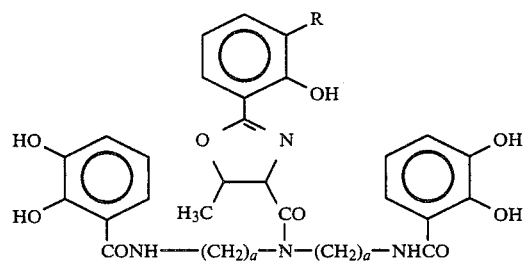

wherein R is H or OH, and
a is 3 or 4.

17. A compound having the structural formula:

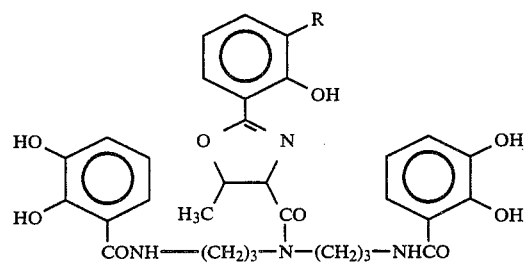

wherein R is H or OH.

18. A compound having the structural formula:

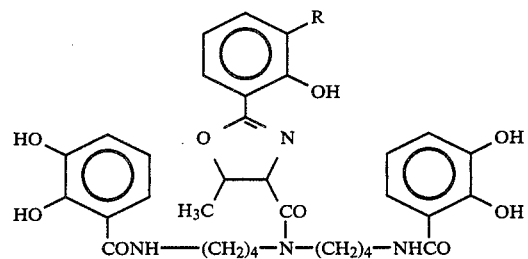

wherein R is H or OH.

* * * * *